United States Patent
Omeis

(10) Patent No.: US 10,214,484 B2
(45) Date of Patent: Feb. 26, 2019

(54) METHOD FOR PREPARING ACROLEIN CYANOHYDRINS

(71) Applicant: Evonik Degussa GmbH, Essen (DE)

(72) Inventor: Marianne Omeis, Dorsten (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/936,868

(22) Filed: Mar. 27, 2018

(65) Prior Publication Data

US 2018/0305303 A1 Oct. 25, 2018

(30) Foreign Application Priority Data

Apr. 21, 2017 (EP) .................................... 17167628

(51) Int. Cl.
| | | |
|---|---|---|
| C07C 255/03 | (2006.01) |
| C07C 255/15 | (2006.01) |
| C07C 253/34 | (2006.01) |
| C07C 409/38 | (2006.01) |
| C07C 29/14 | (2006.01) |
| C07C 253/30 | (2006.01) |
| C07C 253/10 | (2006.01) |
| C07F 9/30 | (2006.01) |
| C07F 9/32 | (2006.01) |

(52) U.S. Cl.
CPC ............ *C07C 255/15* (2013.01); *C07C 29/14* (2013.01); *C07C 253/10* (2013.01); *C07C 253/30* (2013.01); *C07C 253/34* (2013.01); *C07C 409/38* (2013.01); *C07F 9/301* (2013.01); *C07F 9/3211* (2013.01)

(58) Field of Classification Search
CPC .................................................. C07C 255/03
USPC ........................................................ 558/315
See application file for complete search history.

(56) References Cited

U.S. PATENT DOCUMENTS

| | | |
|---|---|---|
| 3,850,976 A | 11/1974 | Shibuya et al. |
| 3,939,050 A | 2/1976 | Kleiner et al. |
| 4,168,963 A | 9/1979 | Rupp et al. |
| 4,218,393 A | 8/1980 | Kröner |
| 4,334,013 A | 6/1982 | Bergthaller et al. |
| 4,336,206 A | 6/1982 | Mündnich et al. |
| 4,521,348 A | 6/1985 | Finke et al. |
| 4,599,207 A | 7/1986 | Lachhein et al. |
| 4,859,784 A | 8/1989 | Effenberger et al. |
| 5,420,329 A | 5/1995 | Zeiss |
| 5,785,942 A | 7/1998 | Hippel et al. |
| 6,096,173 A | 8/2000 | Hippel et al. |
| 6,359,162 B1 | 3/2002 | Willms |
| 8,143,434 B2 | 3/2012 | Gropp et al. |
| 8,334,399 B2 | 12/2012 | Gropp et al. |
| 8,975,440 B2 | 3/2015 | May et al. |
| 2009/0163735 A1 | 6/2009 | Schleep et al. |
| 2009/0299023 A1 | 12/2009 | Gropp et al. |
| 2010/0069594 A1 | 3/2010 | Gropp et al. |
| 2010/0069662 A1 | 3/2010 | Gropp et al. |
| 2011/0306784 A1 | 12/2011 | May et al. |
| 2017/0081349 A1 | 3/2017 | Ressel et al. |

FOREIGN PATENT DOCUMENTS

| | | |
|---|---|---|
| CN | 101 830 926 | 9/2010 |
| CN | 102 372 739 | 3/2012 |
| CN | 102 399 240 | 4/2012 |
| DE | 23 02 523 | 8/1974 |
| DE | 30 47 024 | 7/1982 |
| EP | 0 011 245 | 5/1980 |
| EP | 0 019 227 | 11/1980 |
| EP | 0 019 750 | 12/1980 |
| EP | 0 029 168 | 5/1981 |
| EP | 0 127 877 | 12/1984 |
| EP | 0 377 870 | 7/1990 |
| EP | 0 546 566 | 6/1993 |
| EP | 0 922 675 | 6/1999 |
| EP | 0 941 965 | 9/1999 |
| GB | 1047920 | 11/1966 |
| WO | 2015/173146 | 11/2015 |

OTHER PUBLICATIONS

Piettre, Tetrahedron Letters, 37 (13), 2233-2236.
M. Kriebel: Absorption, 2. Design of Systems and Equipment, Ullmann's Encyclopedia of Industrial Chemistry, Electronic Release, chap. 3, Wiley VCH, Weinheim Oct. 2008.
U.S. Appl. No. 09/209,417, filed Dec. 11, 1998, Hippel et al.
U.S. Appl. No. 09/264,891, filed Mar. 9, 1999, von Hippel at al.
U.S. Appl. No. 12/296,780, filed Oct. 10, 2008, 2009/0163735, Schleep et al.
U.S. Appl. No. 12/517,366, filed Jun. 3, 2009, 2010/0069662, Gropp et al.

*Primary Examiner* — Jeffrey H Murray
(74) *Attorney, Agent, or Firm* — Grüneberg and Myers PLLC

(57) ABSTRACT

The present invention relates to an improved method for preparing acrolein cyanohydrins from hydrocyanic acid and the corresponding acroleins. The method is characterized in that the acrolein cyanohydrins obtained have a very low hydrocyanic acid content or are free of hydrocyanic acid and are therefore particularly well suited as intermediates for the synthesis of glufosinates.

17 Claims, No Drawings

METHOD FOR PREPARING ACROLEIN CYANOHYDRINS

This application claims priority to European Patent Application No. 17167628.1, filed on Apr. 21, 2017, and incorporated herein by reference.

The present invention relates to an improved method for preparing acrolein cyanohydrins from hydrocyanic acid and the corresponding acroleins. The method is characterized so that the acrolein cyanohydrins obtained have a very low hydrocyanic acid content or are free of hydrocyanic acid and are therefore particularly well suited as intermediates for the synthesis of glufosinates.

BACKGROUND OF THE INVENTION

Acrolein cyanohydrins are industrially important raw materials.

An important application of these compounds is the synthesis of phosphinothricin (2-amino-4-[hydroxy(methyl) phosphinoyl]butyric acid, vulgo "glufosinate", or glufosinate salts (EP 0 546 566 A1).

U.S. Pat. Nos. 4,521,348, 4,599,207, 6,359,162 B1, CN 102372739 A, CN 102399240 A, CN 101830926 A describe methods for preparing glufosinates and similar compounds. DE 23 02 523 A1 mentions a similar method in which ethane-1,2-diphosphinic acid diester is obtained from phosphorous acid esters and acetylene, S. R. Piettre, Tetrahedron Letters, 3 (13), 2233-2236 describes similar compounds comprising phosphonyl groups and preparation thereof.

Glufosinates are mainly used as herbicides (EP 0 377 870 A1, U.S. Pat. No. 4,168,963). In addition, EP 0 029 168 A1 mentions the use of similar phosphorus compounds for preparing copolymers in the field of photography.

An essential step in the synthesis of the glufosinates is the addition of a phosphinic acid ester to the double bond of acrolein cyanohydrin ("AcCH" below) or acrolein cyanohydrin acetate ("ACA"). In this reaction in many methods of the prior art, ACA protected by an acetate group is used, obtainable by a method according to EP 0 019 227 A1, e.g. in EP 0 011 245 A1, EP 0 127 877 A2. The reaction using the protected derivative avoids undesired side reactions. On the other hand, it leads to further disadvantages as described in the prior art. WO 2015/173146 A1 discusses the by-products which correlate with the acetylation of the OH function of the cyanohydrin or the omission thereof (WO 2015/173146 A1, page 4, lines 8-24).

In addition, it has already been recognized in DE 30 47 024 A1 that AcCH unprotected on the OH group may also be used in this reaction. Especially when this unprotected AcCH is used as reactant, instead of ACA, the highest possible purity of the same is very important.

AcCH is typically obtained by reaction of acrolein and hydrocyanic acid (U.S. Pat. No. 3,850,976.) The problem which occurs here is that a certain residue of the hydrocyanic acid reactant is always found in the AcCH obtained. This is even more so the case when an excess of hydrocyanic acid is used, based on acrolein, which is customary due to the desired as complete as possible conversion of the acrolein.

This residual content of hydrocyanic acid causes several problems however: for instance, it results in undesired side reactions in the subsequent synthetic sequence. This is especially problematic in the synthesis of glufosinates, and has already been noted in the prior art (WO 2015/173146 A1: page 2, line 15). In addition, hydrocyanic acid is toxic and can react explosively, particularly since a peroxide is present in the subsequent step which leads to release of oxygen. It is therefore also undesirable for the point of view of operational safety that free hydrocyanic acid is present in the AcCH.

The prior art describes several methods for removing the hydrocyanic acid—however these are quite cumbersome or cause further problems. The reason for this is that the treatment of AcCH is problematic and AcCH cannot be simply subjected to customary purification methods due to its instability.

This previous provision of hydrocyanic acid-free AcCH entails the following steps according to conventional methods:
a) acetylation of the crude AcCH contaminated with hydrocyanic acid to ACA and purification (described for example in EP 0 019 750 A1);
b) deacetylation of the ACA via ion exchange (as described in Example 1 of WO 2015/173146 A1, page 17, lines 12-22).

This means that up to now the provision of hydrocyanic acid-free AcCH cannot circumvent the acetylation. The acetic acid released both in the acetylation and in the deacetylation itself leads to further impurities in the AcCH obtained after the deacetylation. These impurities may again lead to side reactions in the subsequent steps of the synthesis.

A further disadvantage of the hydrocyanic acid removal described above is that it is very expensive due to the costly use of an ion exchanger.

There exists a need, particularly in the synthesis of glufosinates, to omit the acetylation of the (intermediate) product AcCH, and still to be able to use this as free of hydrocyanic acid as possible.

Accordingly, the object of the present invention was to provide an improved synthetic route for preparing acrolein cyanohydrin and similar compounds compared to the prior art. This synthesis should lead especially to products having lower impurities, in particular a lowest possible fraction of hydrocyanic acid, and at the same time to avoid the disadvantages of the methods of the prior art.

The invention achieves this object and, surprisingly, shows an efficient alternative way to remove these by-products and to more easily obtain pure AcCH.

DETAILED DESCRIPTION OF THE INVENTION

The present invention accordingly relates to a method for preparing a compound of the formula (I)

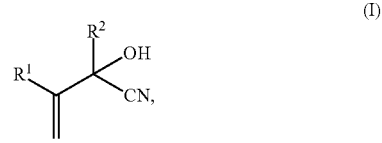

where $R^1$ and $R^2$ are each independently selected from hydrogen, alkyl group, phenyl, benzyl, comprising the following steps:
(a) reacting at least one compound of the formula (II)

with hydrocyanic acid and at least one base B, whereby a crude product CP comprising (I) and hydrocyanic acid is obtained;

b) at least partially removing hydrocyanic acid from the crude product CP by subjecting the latter to stripping, whereby a pure product comprising the compound (I) is obtained, wherein the pure product has a reduced content of hydrocyanic acid compared to CP, characterized in that the stripping is carried out at a pressure of <1 bar, wherein optionally an inert stripping gas is used in countercurrent flow.

$R^1$ and $R^2$ are in particular each independently selected from hydrogen, alkyl group having 1 to 6 carbon atoms, phenyl, benzyl. $R^1$ and $R^2$ are preferably each independently selected from hydrogen, alkyl group having 1 to 6 carbon atoms. More preferably, $R^1$ and $R^2$ are each independently selected from hydrogen, methyl, ethyl. Most preferably, $R^1=R^2$=hydrogen—then the compound of the formula (II) is acrolein and the compound of the formula (I) is acrolein cyanohydrin.

In step a) of the method according to the invention, a compound of the formula (II)

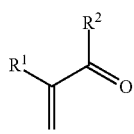

(II)

is reacted with hydrocyanic acid and a base B, whereby a crude product CP comprising (I) and hydrocyanic acid is obtained.

The reaction conditions for this purpose are known to those skilled in the art and can be found, for example, in U.S. Pat. No. 3,850,976.

The hydrocyanic acid may be used as a liquid or in gaseous form, preferably as a liquid.

The reaction of the compound of the structure (II) can be carried out in a reactor with a circulation system. The circulation system ensures an intensive mixing of the critical reactants.

The base B is not further restricted, but it is preferable to select the base B from the group consisting of ammonia, trialkylamine, ammonium salt, more preferable to select from the group consisting of ammonia, trialkylamine, even more preferable to select from the group consisting of ammonia, triethylamine, most preferable to select triethylamine. Ammonia can be used in a mixture with $CO_2$, as described in U.S. Pat. No. 3,850,976.

The preferred trialkylamine is triethylamine.

Preferred ammonium salts are ammonium carbonate, ammonium hydrogencarbonate, ammonium carbamate, particularly preferably ammonium carbonate, ammonium hydrogencarbonate.

Step a) is particularly conducted in this case at a temperature of −50° C. to 80° C., preferably conducted at a temperature of −40° C. to 60° C., more preferably conducted at a temperature of −30° C. to 30° C., even more preferably conducted at a temperature of −10 to 10° C., yet more preferably conducted at a temperature of −5° C. to 5° C.

The amount of hydrocyanic acid used in step a) of the method according to the invention is in principle unrestricted. However, in order to ensure as complete conversion as possible of the compound (II), and since the present invention specifically allows the easy removal of excess hydrocyanic acid in the CP, the hydrocyanic acid in step a) of the method according to the invention is particularly used in an amount of >1 molar equivalent, preferably in an amount of >1 to 10 molar equivalents, more preferably in an amount of 1.01 molar equivalents to 7.5 molar equivalents, even more preferably 1.03 molar equivalents to 5 molar equivalents, even more preferably 1.3 molar equivalents to 2 molar equivalents, based in each case on the amount of all compounds of the formula (II) used in step a).

The amount of base B in step a) is not further limited. The amount of base B in step a) is preferably 0.01 to 5% by weight, more preferably 0.1 to 1% by weight, based on the sum of the weights of hydrocyanic acid used in step a) and all compounds of the formula (III) used in step a).

More preferably, sufficient base B is used in step a) such that the reaction mixture in step a) has a pH of ≤6.9, more preferably 7.0 to 7.5, preferably 7.3 (at 25° C.).

The pH of the reaction mixture in step a) can be determined in a routine manner with appropriate electrodes by those skilled in the art so that the required amount of base B can be determined therefrom. A possible pH electrode is, for example, the "Flushtrode pH electrode A238060" (manufacturer: Hamilton).

The reaction time is not further restricted. The reaction in step a) is carried out until the desired conversion of the compound of the formula (II) with hydrocyanic acid to give the product (I) is attained. In particular, the reaction time is 20 seconds to 3 hours, preferably 1 to 85 minutes.

Step a) of the method according to the invention is carried out with or without, preferably without, solvent. If a solvent is used, this is preferably at least one selected from alcohol, toluene, xylene, methylene chloride, dialkylformamide or dialkyl sulfoxide, more preferably at least one selected from methanol, ethanol, toluene, xylene, methylene chloride.

At the end of step a) a CP is obtained which comprises the target compound (I), and m addition comprises also hydrocyanic acid. The proportion of hydrocyanic acid is dependent on the excess of hydrocyanic acid which was used in step a) of the method according to the invention and also on the conversion in step a). In particular, the proportion of hydrocyanic acid in the CP, based on the amount of compound of the formula (I) in the CP, is up to 10% by weight, preferably is in the range of 3 to 4% by weight.

This crude product CP can now be supplied to step b), i.e. the stripping according to the invention.

It is of advantage, however, that the CP is stabilized before carrying out step b). Stabilization according to the invention signifies that the crude product CP is mixed with at least one acid such that after mixing with the acid it has a pH of <6.9, preferably a pH of <5.0, more preferably <4.0, even more preferably <3.0, still more preferably <2.0, especially preferably <1.0 (at 25° C.).

The pH of the mixture thus stabilized can be determined in a routine manner with appropriate electrodes by those skilled in the art so that the required amount of acid can be determined therefrom. A possible pH electrode is, for example, the "Flushtrode pH electrode A238060" (manufacturer: Hamilton).

The amount of acid mixed with the CP for the stabilization is preferably ≤10% by weight, preferably ≤5% by weight, more preferably ≤1% by weight, even more preferably ≤0.1% by weight, based on the amount of all compounds of the formula (I) in the CP.

The required acid used for this purpose is preferably selected from the group consisting of mineral acids, alkylcarboxylic acid, aromatic sulfonic acid, or mixtures of aromatic sulfonic acid and alkylcarboxylic acid.

A preferred alkylcarboxylic acid is acetic acid.

A preferred mineral acid is phosphoric acid.

"Aromatic sulfonic acid" signifies that the aromatic radical in this sulfonic acid may bear, or also may not bear, alkyl substituents. Preferred aromatic sulphonic acids are selected from benzenesulfonic acid and alkyl-substituted benzenesulfonic acids, wherein the alkyl substituents preferably have 1 to 20 carbon atoms and the phenyl ring preferably bears only one para-alkyl substituent, such as para-toluenesulfonic acid.

If mixtures of aromatic sulfonic acid and alkylcarboxylic acid are used for stabilizing the CP, all aromatic sulfonic acids and all carboxylic acids in these mixtures are, in particular, present in the following ratios by weight: weight of all aromatic sulfonic acids to all alkylcarboxylic acids=9:1 to 1:9, preferably from 8:2 to 2:8, more preferably from 7:3 to 3:7, even more preferably from 6:4 to 4:6, most preferably 1:1.

The CP obtained after step a), be it now stabilized or not further stabilized, it preferably being stabilized, is then subjected to step b).

In step b), the at least partial removal of hydrocyanic acid from the crude product CP is carried out, by subjecting the latter to stripping, whereby a pure product comprising the compound (I) is obtained, wherein the pure product has a reduced content of hydrocyanic acid compared to CP.

This was surprising since acrolein cyanohydrin and similar compounds in combination with hydrocyanic acid are highly explosive in the presence of oxygen, as is to be expected in the next step (Gestis Substance Database of the Institute for Occupational Safety). According to specialist expertise, these mixtures are not in principle amenable to purification by distillation since an acidic stabilization must be ensured at all times and, furthermore, the thermal stability of the product is not sufficient to carry out evaporation under industrially accessible vacuum conditions.

In the method according to the present invention, the CP from step a) (stabilized or non-stabilized, preferably stabilized) is then subjected to stripping in step b). It has been established, surprisingly, that with this method a particularly mild removal of the hydrocyanic acid is possible.

"Stripping" is a physical separation process known to those skilled in the art which is used in many fields in the prior art for purifying liquids (described for example in M. Kriebel: "Absorption, 2. Design of Systems and Equipment". Ullmann's Encyclopedia of Industrial Chemistry, Electronic Release, chap. 3, Wiley V C H, Weinheim October 2008). In this case, a gas phase is contacted in countercurrent flow with a phase to be purified or the phase to be purified is contacted at reduced pressure of less than 1 bar with or without countercurrent flow. In accordance with the invention, this contacting occurs in particular in a column.

In the present invention, the stripping is conducted at a reduced pressure of <1 bar. Optionally, an inert stripping gas may be used in countercurrent flow, which means that, in order to assist the stripping, such an inert stripping gas may be introduced into the column in countercurrent flow to the CP, provided the pressure remains <1 bar.

"Wherein optionally an inert stripping gas is used in countercurrent flow" accordingly signifies that, to assist the stripping, such an inert stripping gas is introduced into the column in countercurrent flow to the CP comprising hydrocyanic acid and the compound of the formula (I) introduced into the column, and the pressure herein remains <1 bar, or even that no such inert stripping gas is introduced.

Preference is given to the procedure without inert stripping gas.

The temperature of the stripping can be adjusted by setting an appropriate negative pressure in the column in a routine manner by those skilled in the art.

The pressure in step b) according to the invention is <1 bar, is in particular in the range of 1-500 mbar, more preferably in the range of 10-200 mbar.

It is preferred in this case that a temperature of 85° C. or less is maintained during the stripping, since it was established, surprisingly, that a particularly mild and advantageous purification of AcCH is possible at a temperature of 85° C. or less. Preferably, the temperature is ≤72.5° C., more preferably in a range of −10° C. to 70° C., more preferably in a range of −5° C. to 30° C.

The purification of the CP can be improved by increasing the surface area of the same. Preferably, for this purpose, the CP In step b) of the method according to the invention is passed at least partially over a bed of packing elements or over a structured packing. Of suitability for this purpose are all packing elements and structured packings which are known to the person skilled in the art from the prior art for distillations and for absorption processes. Alternatively, the stripping can be carried out in a falling-film or thin-film evaporator. These apparatuses are known from the prior art to those skilled in the art.

Preferred inert stripping gas is nitrogen.

If an inert stripping gas is used, the water content of the same should be low, preferably <1% by volume, more preferably <0.1% by volume.

A pure product is then obtained in step b) according to the invention which, compared to the CP, has a reduced hydrocyanic acid content. This pure product typically comprises a hydrocyanic acid content of <0.1% by weight, based on the compound of the formula (I) in the pure product.

A further step c) then preferably follows on from step b) of the method according to the invention. Accordingly, the present invention relates, also together with steps a) and b) described above, to a method for preparing a compound of the formula (III)

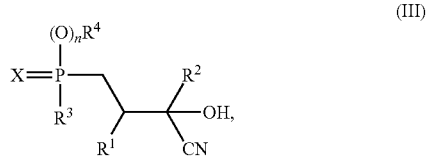

where $R^1$ and $R^2$ are as defined above,
$R^3$, $R^4$ are each independently selected from (halo)alkyl, (halo)aryl, (halo)aralkyl, (halo)cycloalkyl,
X is oxygen or sulfur,
n=0 or 1;
comprising the steps a) and b) according to the method according to the invention for preparing a compound of the formula (I) and additionally comprising the step c), in which the pure product comprising the compound (I) obtained in step b), wherein the pure product has a reduced content of hydrocyanic acid compared to CP, is reacted with a compound of the formula (IV).

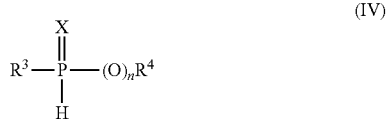

This reaction may be effected by methods known to those skilled in the art (described in WO 2015/173146 A1). By using the pure product comprising the compound (I) obtained in step b), and a reduced hydrocyanic acid content, fewer side reactions occur in step c). The risk of explosions, which is present due to hydrocyanic acid and free-radical-forming substance in step c), is likewise reduced.

The temperature in the reaction in step c) is preferably from 50° C. to 105° C., more preferably from 60° C. to 95° C., even more preferably from 65° C. to 90° C.

$R^3$, $R^4$ are preferably each independently selected from (halo)alkyl having 1 to 12 carbon atoms, (halo)aryl having 6 to 10 carbon atoms, (halo)aralkyl having 7 to 10 carbon atoms, (halo)cycloalkyl having 4 to 10 carbon atoms.

(Halo)alkyl according to the invention signifies alkyl or haloalkyl.

(Halo)aryl according to the invention signifies aryl or haloaryl.

(Halo)aralkyl according to the invention signifies aralkyl or haloaralkyl.

(Halo)cycloalkyl according to the invention signifies cycloalkyl or halocycloalkyl.

$R^3$ is preferably selected from alkyl having 1 to 4 carbon atoms, haloalkyl having 1 to 4 carbon atoms, more preferably methyl or ethyl, more preferably methyl.

$R^4$ is preferably selected from alkyl having 1 to 6 carbon atoms, haloalkyl having 1 to 6 carbon atoms, more preferably selected from alkyl having 3 to 6 carbon atoms, more preferably selected from alkyl having 4 or 5 carbon atoms, most preferably n-butyl or n-pentyl.

Additionally in step c), a free-radical-forming substance is preferably used. This is preferably a free-radical former of the formula (V)

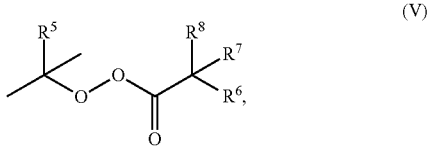

where $R^5$ is methyl, ethyl, 2,2-dimethylpropyl or phenyl, $R^6$, $R^7$ are each independently an alkyl group having 1 to 10 carbon atoms, preferably 2 to 6, more preferably 1 to 4 carbon atoms, and
$R^8$ is hydrogen or an alkyl group having 1 to 10 carbon atoms, preferably hydrogen or an alkyl group having 1 to 6 carbon atoms, more preferably hydrogen or an alkyl group having 1 to 4 carbon atoms.

The free-radical formers of the formula (V) are known per se and in some cases commercially available.

The free-radical former of the formula (V) is preferably selected here from the group consisting of tert-butyl peroxypivalate, tert-amyl peroxypivalate, tert-butyl peroxyneodecanoate, 1,1,3,3-tetramethylbutyl peroxyneodecanoate, tert-butyl peroxy-2-ethylhexanoate, 1,1,3,3-tetramethylbutyl peroxy-2-ethylhexanoate, tert-amyl peroxyneodecanoate, cumyl peroxyneodecanoate, cumyl peroxyneoheptanoate, cumyl peroxypivalate, and mixtures thereof.

The free-radical former of the formula (V) is preferably selected here from the group consisting of tert-butyl peroxyneodecanoate, 1,1,3,3-tetramethylbutyl peroxyneodecanoate, tert-butyl peroxy-2-ethylhexanoate, 1,1,3,3-tetramethylbutyl peroxy-2-ethylhexanoate, cumyl peroxyneodecanoate, and mixtures thereof, with particular preference in turn being given to 1,1,3,3-tetramethylbutyl peroxyneodecanoate, tert-butyl peroxyneodecanoate and/or tert-butyl peroxy-2-ethylhexanoate.

In particular, the free-radical formers specified as preferred enable a very good reaction regime under mild reaction conditions, particularly in the temperature range specified as preferred, whereby the desired compounds of the formula (III) may be obtained so high yields and high purity.

In step c) of the method according to the invention, in total 0.1 to 10 mol %, preferably 0.25 to 7 mol %, further preferably 0.5 to 7 mol %, particularly preferably 0.5 to 5 mol %, of free-radical formers of the formula (V) are used, based on the total amount of all compounds of the formula (I) which are present in the pure product and are used in step c) of the method according to the invention.

Further preferred conditions of the reaction in step c) are known to those skilled in the art and can be found, for example, in WO 2015/173146 A1.

The examples which follow are intended to elucidate the invention, but without restricting it thereto.

EXAMPLES

1. Preparation of Crude AcCH (Step a)

1.1 50 g of acrolein as a liquid are mixed with stirring and reacted with 1.3 mol equivalents of hydrocyanic acid, and sufficient triethylamine such that the pH of the mixture is 7.3, in a double-jacketed reactor at −5° C. The reactants and the catalyst are metered in continuously over 2 hours in order to limit the exothermicity. After a reaction time of 2 hours, a mixture of para-toluenesulfonic acid and acetic acid (ratio by weight 1:1) are added to the reaction mixture until the pH goes below pH 3. This crude product comprises ~30 mol % hydrocyanic acid based on acrolein cyanohydrin.

1.2 For comparison, an attempt is made to obtain crude AcCH by the method described in U.S. Pat. No. 3,850,976, Example 1. This method, however, comprises a step of the distillation of AcCH under reduced pressure (65° C., 3 mm). This step is manageable under laboratory conditions but is not feasible for larger batches. This method is therefore excluded from industrial scale batches and even for small batches represents a safety risk.

2. Purification of the Crude Product from 1 (Step b)

The AcCH crude product, obtained according to step 1.1, is pre-heated with the aid of a Telab pump and an external thermostat to a temperature of 30-72.5° C. and is fed in amounts of 10-50 g/h to the top of a 30 cm length heatable stripping column. A reduced pressure of 10-200 mbar is applied to the column.

The column comprises a metal mesh according to the prior art which satisfactorily simulates regulated packings used in production.

According to experience, 10 cm of this metal mesh corresponds to 5 theoretical plates.

The column is heated but only to compensate for heat losses and to maintain the column at the temperature slated.

A reflux divider is located on the column with which the ratio of return stream and off-take may be adjusted. A condenser is also integrated with which vapours are condensed. The vapours in this case consist largely of condensed hydrocyanic acid. The distillate receiver container may contain phosphoric acid in order to ensure sufficient stabilization of the condensed hydrocyanic acid.

In laboratory methods, the hydrocyanic acid is neutralized with aqueous sodium hydroxide solution and sent for regulated disposal.

In more recent production methods, this may be incinerated or recycled.

The hydrocyanic acid-free acrolein cyanohydrin is discharged with the aid of a pump at the same amount per unit time as the feed to the column. In this way, the liquid phase level remains constant and thermal stress on the material is time-limited.

The distillation is heated via a double-jacketed boiler.

The hydrocyanic acid-free acrolein cyanohydrin in the bottoms is analyzed with respect to residual cyanide traces by argentometric titration with sliver nitrate solution.

It shows an exceptionally low amount of less than 0.1% by weight of hydrocyanic acid, based on the acrolein cyanohydrin in the pure product thus purified.

It has been established that, on increasing the pressure to ≥1 bar, purification of the AcCH on an industrial scale is not feasible since it results in uncontrolled thermal decomposition. This is readily controllable in the pressure range of 10-200 mbar.

The invention claimed is:

1. A method for preparing a compound of formula (I)

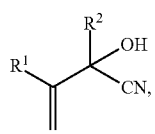

the method comprising:
(a) reacting at least one compound of the formula (II)

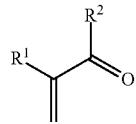

with hydrocyanic acid and at least one base B, whereby a crude product CP comprising the compound of formula (I) and hydrocyanic acid is obtained; and
(b) at least partially removing hydrocyanic acid from the crude product CP by subjecting the latter to stripping, whereby a pure product comprising the compound (I) is obtained, wherein the pure product has a reduced content of hydrocyanic acid compared to CP,
wherein the stripping is carried out at a pressure of <1 bar, wherein optionally an inert stripping gas is used in countercurrent flow, and
wherein $R^1$ and $R^2$ are each independently hydrogen, an alkyl group, phenyl, or benzyl.

2. The method according to claim 1, wherein $R^1$ and $R^2$ are each independently hydrogen, an alkyl group having 1 to 6 carbon atoms, phenyl, or benzyl.

3. The method according to claim 1, wherein $R^1$ and $R^2$ are each hydrogen.

4. The method according to claim 1, wherein the base B is at least one member selected from the group consisting of ammonia, a trialkylamine, and an ammonium salt.

5. The method according to claim 1, wherein said a) reacting is conducted at a temperature of from 50° C. to 80° C.

6. The method according to claim 1, wherein the hydrocyanic acid in said a) reacting is present in an amount of >1 molar equivalent, based on the amount of all compounds of the formula (II) present in said a) reacting.

7. The method according to claim 1, wherein the amount of base B in said a) reacting is 0.01 to 5% by weight, based on the sum of the weights of hydrocyanic acid present in said a) reacting and all compounds of the formula (II) present in step said a) reacting.

8. The method according to claim 1, wherein the crude product CP is mixed prior to the at least partially removing of b) with at least one acid so that, after mixing with the acid, CP has a pH of <6.9.

9. The method according to claim 8, wherein the at least one acid has a pKa of ≤1.

10. The method according to claim 8, wherein the acid is at least one member selected from the group consisting of mineral acid, an alkylcarboxylic acid, and an aromatic sulfonic acid.

11. The method according to claim 1, wherein a temperature of ≤85° C. is maintained during the stripping in the at least partially removing of b).

12. The method according to claim 1, wherein the crude product CP during the stripping in the at least partially removing of b) is passed at least partially over a bed of packing elements or over a structured packing.

13. The method according to claim 1, further comprising, after b):
c) reacting the pure product comprising the compound (I) obtained in b), wherein the pure product has a reduced content of hydrocyanic acid compared to CP, with a compound of the formula (IV)

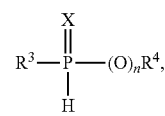

to obtain a compound of the formula (III)

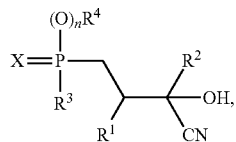

wherein $R^3$, $R^4$ are each independently an (halo)alkyl group, an (halo)aryl group, a (halo)aralkyl group, or a (halo)cycloalkyl group,
wherein X is oxygen or sulfur, and
wherein n=0 or 1.

14. The method according to claim 13, wherein the reaction in said c) reacting is conducted at a temperature of 50° C. to 105° C.

15. The method according to claim 13, wherein each of $R^3$ and $R^4$ is, independently, a (halo)alkyl group having 1 to 12 carbon atoms, a (halo)aryl group having 6 to 10 carbon atoms, a (halo)aralkyl group having 7 to 10 carbon atoms, or a (halo)cycloalkyl group having 4 to 10 carbon atoms.

16. The method according to claim 13, wherein
at least one free-radical-forming substance is present in said c) reacting.

17. The method according to claim 16, wherein
the free-radical-forming substance is a free-radical initiator of the formula (V)

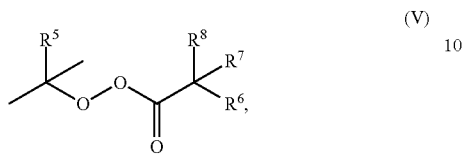

(V)

wherein $R^5$ is methyl, ethyl, 2,2-dimethylpropyl, or phenyl, wherein $R^6$, $R^7$ are each independently an alkyl group having 1 to 10 carbon atoms, and wherein $R^8$ is hydrogen or an alkyl group having 1 to 10 carbon atoms.

* * * * *